United States Patent
Moriya

(10) Patent No.: US 7,633,617 B2
(45) Date of Patent: Dec. 15, 2009

(54) DEFECTIVE PARTICLE MEASURING APPARATUS AND DEFECTIVE PARTICLE MEASURING METHOD

(75) Inventor: Kazuo Moriya, Tokyo (JP)

(73) Assignee: Raytex Corporation, Tokyo (JP)

(*) Notice: Subject to any disclaimer, the term of this patent is extended or adjusted under 35 U.S.C. 154(b) by 330 days.

(21) Appl. No.: 11/883,510

(22) PCT Filed: Feb. 3, 2006

(86) PCT No.: PCT/JP2006/001882

§ 371 (c)(1),
(2), (4) Date: Aug. 1, 2007

(87) PCT Pub. No.: WO2006/082932

PCT Pub. Date: Aug. 10, 2006

(65) Prior Publication Data

US 2008/0111992 A1 May 15, 2008

(30) Foreign Application Priority Data

Feb. 3, 2005 (JP) ............... 2005-027941

(51) Int. Cl.
*G01N 15/02* (2006.01)
(52) U.S. Cl. ............... 356/336; 356/339
(58) Field of Classification Search ......... 356/335–343, 356/614; 250/574
See application file for complete search history.

(56) References Cited

U.S. PATENT DOCUMENTS 4,456,513 A * 6/1984 Kawai et al. ............. 204/549
5,428,655 A * 6/1995 Moriya et al. ............. 378/4
5,471,298 A * 11/1995 Moriya ............. 356/336
5,644,388 A * 7/1997 Maekawa et al. ............. 356/73

FOREIGN PATENT DOCUMENTS

DE         100 27 780 A1      1/2001

(Continued)

OTHER PUBLICATIONS

International Search Report for PCT/JP2006/301882 mailed May 16, 2006.

*Primary Examiner*—Hoa Q Pham
(74) *Attorney, Agent, or Firm*—Nixon & Vanderhye P.C.

(57) ABSTRACT

A defective particle measuring apparatus that irradiates focused laser light on a sample, images scattered light from the sample, and measures defective particles in the sample based on the image result, includes a position deviation computing portion which, based on an in-plane intensity distribution of scattered light of each defective particle that is imaged, obtains a deviation from a focal point position on an image point side of the scattered light of each defective particle and calculates a position deviation amount in a depth direction of the defective particle corresponding to the deviation from the focal point position, a light intensity correcting portion for correcting the light intensity of the scattered light of the defective particle corresponding to the position deviation amount in the depth direction, and a size determining portion for determining the defective particle size based on the light intensity corrected by the light intensity correcting portion. Thus, the size of the defective particles can be determined at a high precision by a simple constitution in a short time, and density distribution of the defective particles can be obtained.

12 Claims, 14 Drawing Sheets

FOREIGN PATENT DOCUMENTS

| | | |
|---|---|---|
| EP | 0 887 621 A1 | 12/1998 |
| JP | 01-151243 | 6/1989 |
| JP | 06-094595 | 4/1994 |
| JP | 07-072090 | 3/1995 |
| JP | 9-64136 | 3/1997 |
| JP | 11-148903 | 6/1999 |
| JP | 3190157 | 5/2001 |
| JP | 2002-71564 | 3/2002 |
| JP | 3536203 | 3/2004 |
| WO | 97/35162 | 9/1997 |

* cited by examiner

20 μm

20 μm

POSITION DEVIATION = 0
SPREAD OF OBSERVED IMAGE = 2.4 MICRONS

POSITION DEVIATION = 4 MICRONS
SPREAD OF OBSERVED IMAGE = 5.6 MICRONS

POSITION DEVIATION = 8 MICRONS
SPREAD OF OBSERVED IMAGE = 13 MICRONS

POSITION DEVIATION = 20 MICRONS
SPREAD OF OBSERVED IMAGE = 34 MICRONS

| POSITION DEVIATION AMOUNT (μm) | CORRECTION COEFFICIENT |
|---|---|
| 0 | 1 |
| 1 | 1.1 |
| ⋮ | ⋮ |

26b

DEFECTIVE PARTICLE MEASURING APPARATUS AND DEFECTIVE PARTICLE MEASURING METHOD

This application is the US national phase of international application PCT/JP2006/301882 filed 3 Feb. 2006 which designated the U.S. and claims benefit of JP 2005-027941, dated 3 Feb. 2005, the entire content of which is hereby incorporated by reference.

TECHNICAL FIELD

The present invention relates to a defective particle measurement apparatus and a defective particle measuring method that irradiate focused laser light on a sample, image scattered light from the sample, and measure defective particles in the sample based on the image result.

BACKGROUND ART

There have conventionally been apparatuses that irradiate focused laser light on a sample, image scattered light from the sample, perform predetermined image processing on the picked up image, and measure the density distribution of defective particles in the sample based on the image processing result (refer to Patent Document 1). According to this method, as shown in FIG. 3 or FIG. 4, a two-dimensional image is obtained using the 90-degree scattering method by which it is possible to know the two-dimensional placement of defective particles by imaging the laser light that is scattered by the defective particles in the sample.

Patent Document 1: JP 2604607 (Japanese unexamined patent application, First Publication, No. 01-151243)

Patent Document 2: JP 2832269 (Japanese unexamined patent application, First Publication, No. 06-094595)

With a defective particle of a large size, the effective scattering cross-sectional area that scatters the incident laser light is large, and therefore the scattering intensity is large. For this reason, in a defective particle scattering image in which the scattering intensity is large, the defective particle can generally be determined to be one having a large size.

However, laser light that is incident on the sample has a light intensity distribution on a plane that is perpendicular to the axis of incidence of the laser light. Therefore, even for defective particles of the same size, the scattering intensity from a defective particle that is located away from the axis of incidence decreases compared to the scattering intensity from a defective particle that is in the vicinity of the axis of incidence. For this reason, even if only the scattering intensity of the defective particle scattering images is measured, the size of the defective particle cannot be determined. That is, the defective particle scattering image and the defective particle size do not directly correspond.

For example, FIG. 18 shows a scattering intensity distribution when the beam diameter of the incident laser light is 8 μm. Defective particle SB lies on the axis of incidence, while defective particle SA is located 8 μm away from the axis of incidence. The defective particle SA is large and has a scattering efficiency that is 100 times that of the defective particle SB. Curve LA is the scattering intensity distribution of the defective particle SA, and curve LB is the scattering intensity distribution of the defective particle SB. In this case, even though the sizes of the defective particles SA and SB differ by 100 times, the measured scattering intensities are approximately 7, and thus the same scattering intensity. Therefore, it is not possible to determine the size of the defective particles only by the scattering intensity.

For this reason, in the three-dimensional particle detection method disclosed in Patent Document 2, the sample is shifted in the depth direction and a plurality of the defective particle scattering images obtained in Patent Document 1 are acquired as cross-sectional images. By subjecting these cross-sectional images to three-dimensional image processing, the nonuniformity in the optical intensity distribution that is input is corrected, and the size of each defective particle is determined.

However, since it is necessary to obtain a plurality of cross-sectional images in the method that is disclosed in Patent Document 2, the problem arises of the measurement taking time.

DISCLOSURE OF INVENTION

The present invention has been made in consideration of the above circumstances, and has as its object to provide a defective particle measurement apparatus and a defective particle measurement method that can determine the size of defective particles in a short time with high precision using a simple constitution and can determine the density distribution of defective particles.

In order to solve the aforementioned problems and achieve the above object, in a defective particle measuring apparatus that irradiates focused laser light on a sample, images scattered light from the sample, and measures defective particles in the sample based on the image result, the defective particle measuring apparatus of the present invention includes a position deviation computing means which, based on an in-plane intensity distribution of scattered light of each defective particle that is imaged, obtains a deviation from a focal point position on an image point side of the scattered light of the each defective particle and calculates a position deviation amount in a depth direction of the defective particle corresponding to the deviation from the focal point position, the defective particle measuring apparatus measuring characteristics of the defective particle based on the position deviation amount that is calculated by the position deviation computing means.

Also, in a defective particle measuring apparatus that irradiates focused laser light on a sample, images scattered light from the sample, and measures defective particles in the sample based on the image result, the defective particle measuring apparatus of the present invention includes: a position deviation computing means which, based on an in-plane intensity distribution of scattered light of each defective particle that is imaged, obtains a deviation from a focal point position on an image point side of the scattered light of the each defective particle and calculates a position deviation amount in a depth direction of the defective particle corresponding to the deviation from the focal point position; a light intensity correcting means which corrects the light intensity of the scattered light of the defective particle corresponding to the position deviation amount in the depth direction; and a size determining means which determines the size of the defective particle based on the light intensity corrected by the light intensity correcting means.

Also, in a defective particle measuring apparatus that irradiates focused laser light on a sample, images an in-plane intensity distribution of scattered light from within the sample, and measures defective particles in the sample, the defective particle measuring apparatus of the present invention includes: a position deviation computing means which, based on an in-plane intensity distribution of scattered light of each defective particle that is imaged, obtains a deviation from a focal point position on an image point side of the scattered light of the each defective particle and calculates a position deviation amount in a depth direction of the defective particle corresponding to the deviation from the focal point position; and a density computing means that divides the position deviation amount in the depth direction into a plurality of ranges, obtains the number of defective particles that exist within each range, and computes a distribution density of the defective particles in the depth direction from a focal point position on an object point side of an imaging optical system.

Also, in the defective particle measuring apparatus of the present invention, the position deviation computing means may obtain the in-plane intensity distribution of the scattered light approximated to a Gaussian distribution.

Also, in a defective particle measuring method that irradiates focused laser light on a sample, images scattered light from the sample, and measures defective particles in the sample based on the image result, the defective particle measuring method of the present invention includes position deviation computing steps of: obtaining a deviation from a focal point position on an image point side of scattered light of each defective particle based on an in-plane intensity distribution of the scattered light of the each defective particle that is imaged; and calculating a position deviation amount in a depth direction of the defective particle corresponding to the deviation from the focal point position, characteristics of the defective particle being measured based on the position deviation amount that is calculated by the position deviation computing steps.

Also, in a defective particle measuring method that irradiates focused laser light on a sample, images scattered light from the sample, and measures defective particles in the sample based on the image result, the defective particle measuring method of the present invention includes: position deviation computing steps of obtaining a deviation from a focal point position on an image point side of scattered light of each defective particle based on an in-plane intensity distribution of the scattered light of the each defective particle that is imaged, and calculating a position deviation amount in a depth direction of the defective particle corresponding to the deviation from the focal point position; a light intensity correcting step of correcting light intensity of the scattered light of the defective particle corresponding to the position deviation amount in the depth direction; and a size determining step of determining a size of the defective particle based on the light intensity corrected by the light intensity correcting step.

Also, in a defective particle measuring method that irradiates focused laser light on a sample, images an in-plane intensity distribution of scattered light from within the sample, and measures defective particles in the sample, the defective particle measuring method of the present invention includes: position deviation computing steps of obtaining a deviation from a focal point position on an image point side of scattered light of each defective particle based on an in-plane intensity distribution of the scattered light of the each defective particle that is imaged, and calculating a position deviation amount in a depth direction of the defective particle corresponding to the deviation from the focal point position; and density computing steps of dividing the position deviation amount in the depth direction into a plurality of ranges, obtaining the number of defective particles that exist within each range, and computing a distribution density of the defective particles in the depth direction from a focal point position on an object point side of an imaging optical system.

Also, in the defective particle measuring method of the present invention, the position deviation computing steps may include obtaining the in-plane intensity distribution of the scattered light approximated to a Gaussian distribution.

In the defective particle measuring apparatus and defective particle measuring method of the present invention, a position deviation computing means, based on an in-plane intensity distribution of scattered light of each defective particle that is imaged, obtains a deviation from a focal point position on an image point side of the scattered light of the each defective particle and calculates a position deviation amount in a depth direction of the defective particle corresponding to the deviation from the focal point position, a light intensity correcting means corrects the light intensity of the scattered light of the defective particle corresponding to the position deviation amount in the depth direction, a size determining means determines the size of the defective particle based on the light intensity corrected by the light intensity correcting means, and moreover a density computing means divides the position deviation amount in the depth direction into a plurality of ranges, obtains the number of defective particles that exist within each range, and computes a distribution density of the defective particles in the depth direction from a focal point position on an object point side of an imaging optical system. Therefore, it is possible to determine the size of defective particles in a short time with high precision using a simple constitution of acquiring, for example, only one two-dimensional defective particle image and possible to obtain the density distribution of the defective particles.

DESCRIPTIONS OF REFERENCE NUMBERS

Figure 1:
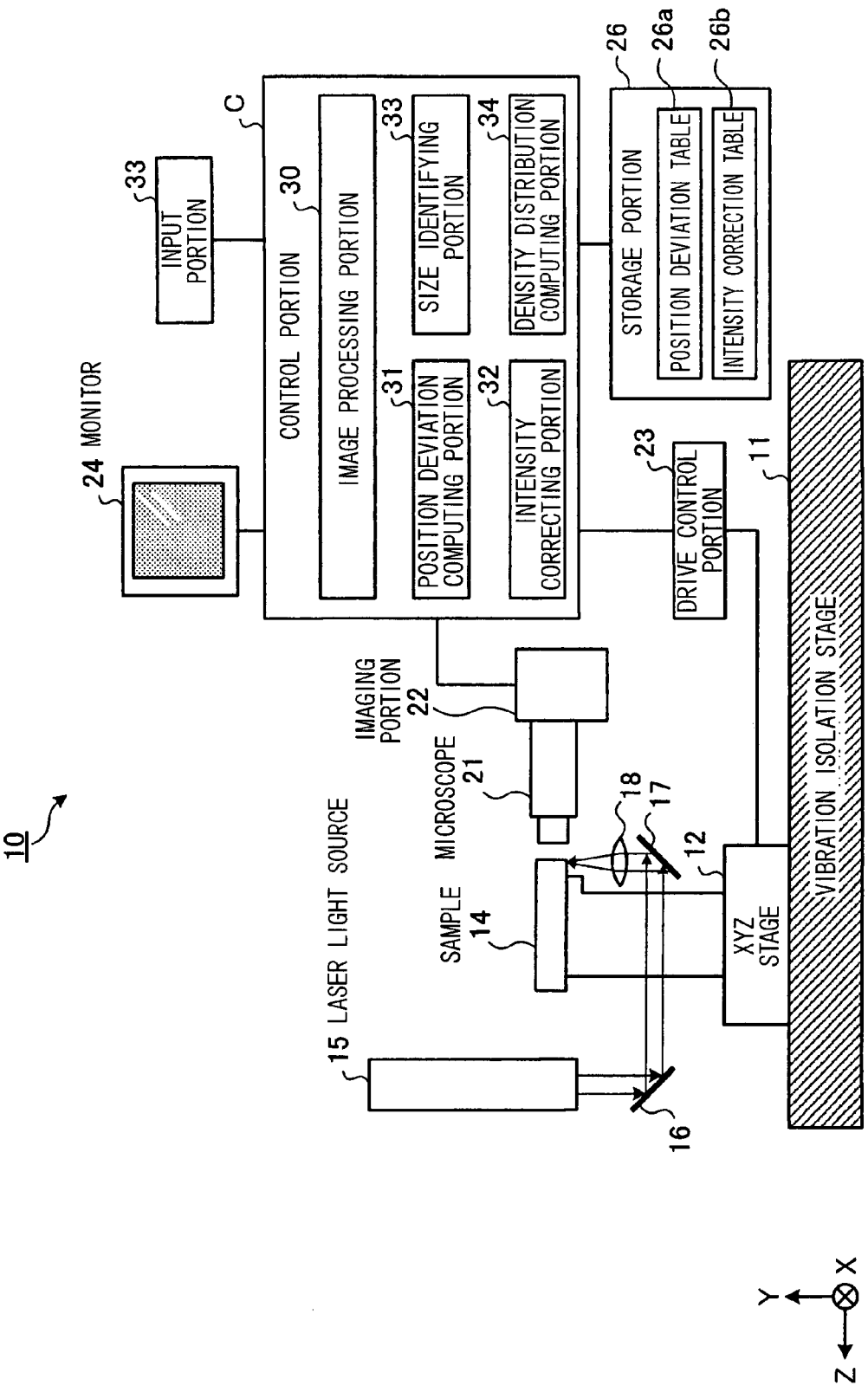
FIG. 1 is a block diagram showing the constitution of a defective particle measuring apparatus, according to an embodiment of the present invention.

10 defective particle measuring apparatus
11 vibration isolation stage
12 XYZ stage
13 sample stage
14 sample
15 laser light source
16, 17 mirror
18 converging lens
21 microscope
22 imaging portion
23 drive control portion
24 monitor
25 input portion
26 storage portion
26a a position deviation table
26b intensity correction table
30 image processing portion
31 position deviation computing portion
32 intensity correcting portion
33 size determining portion
34 density distribution computing portion
42 two-dimensional defective particle image
43 defective particle image
50 defective particle
51 optical system
52 imaging element
C control portion

BEST MODE FOR CARRYING OUT THE INVENTION

Hereinbelow, a defective particle measuring apparatus and a defective particle measuring method that are the best mode for carrying out the present invention shall be described.

FIG. 1 is a block diagram showing the constitution of a defective particle measuring apparatus that is an embodiment of the present invention. In FIG. 1, a defective particle measuring apparatus 10 has an XYZ stage 12 disposed on a vibration isolation stage 11, and a sample 14 such as a semiconductor wafer disposed on the XYZ stage 12 via a sample stage 13. Laser light that is emitted from a laser light source 15 is irradiated via mirrors 16 and 17 and a condenser lens 18 from the Y direction of the sample 14. The laser light that is irradiated is scattered by defective particles in the sample 14, and a defective particle image is imaged by an imaging portion 22 via an optical system that is realized by a microscope 21 disposed in the −Z direction.

Figure 2:
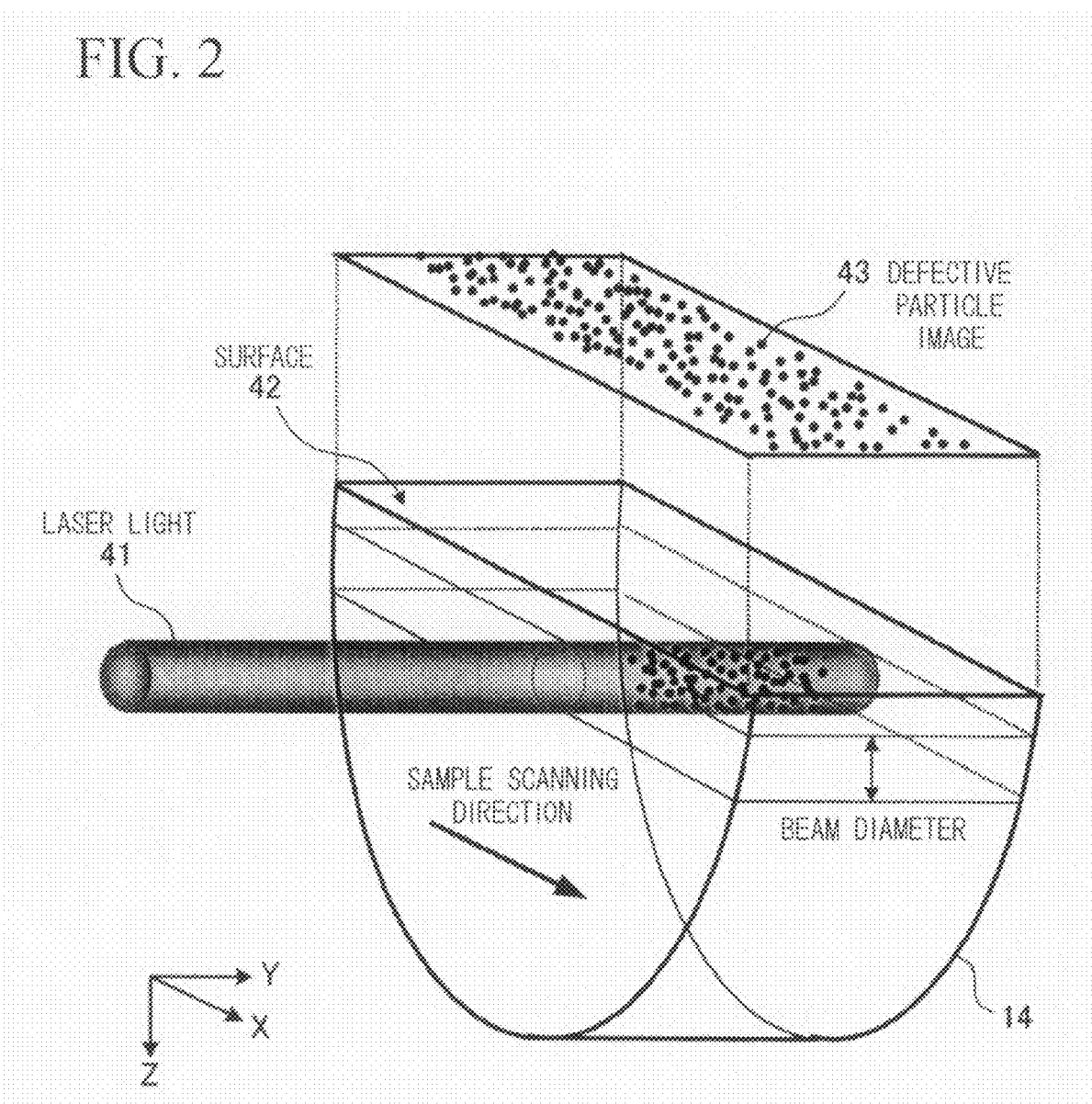
FIG. 2 is a view describing the principle of the 90 degree scattering method.
Figure 3:
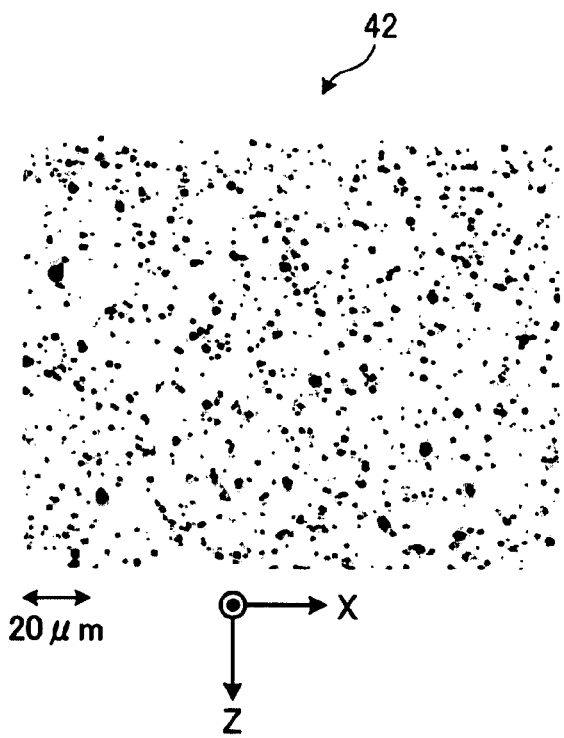
FIG. 3 is a view showing an example of a two-dimensional defective particle image in which defective particles are distributed nearly uniformly.
Figure 4:
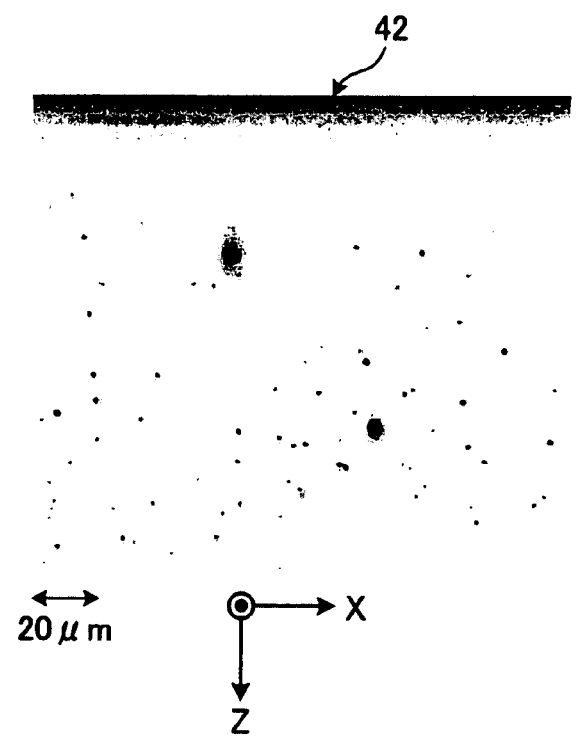
FIG. 4 is a view showing an example of a two-dimensional defective particle image in which different types of defective particles exist.

As shown in FIG. 2, laser light 41 that is converged from the Y direction is input to the sample 14, and the laser light that is scattered by a defective particle is imaged as a defective particle image 43. Here, the XYZ stage 12 moves in the X direction to scan one line portion of the laser light 41 with respect to the sample 14. When the scanning of 1 line in the X direction is complete, the XYZ stage 12 moves in the Z direction in a unit of the beam diameter, and the scanning of the following lines is performed in sequence. Thereby, two-dimensional defective particle images 42 are obtained by scanning the XY plane. FIG. 3 and FIG. 4 are views showing examples of two-dimensional defective particle images. In FIG. 3, defective particle images of a nearly uniform size evenly exist, while in FIG. 4 there exist two large defective particles of a different type.

A control portion C that is realized by a CPU or the like controls the imaging by the imaging portion 22 and controls a drive control portion 23 of a drive portion 23 that drives the XYZ stage 12. Also, a monitor 24, an input portion 25, and a storage portion 26 are connected to the control portion C. The monitor 24, which is realized by a liquid crystal display or the like, displays the measurement result by the control portion C. The input portion 25, which is realized by a mouse and keyboard or the like, is used to input various information and instructions to the control portion C. The storage portion 26 is stored various information that is used for control processes of the control portion C, and in particular stored a position deviation table 26a and an intensity correction table 26b.

The control portion C has an image processing portion 30. The image processing portion 30 acquires a two-dimensional defective particle image that consists of imaged defective particle images in pixel units corresponding to the scan, and performs various image processes. A position deviation computing portion 31 computes the distance from the focal point position on an object point side of the microscope 21 to a defective particle based on the spread of a point image on the image point side in the focal point position of the microscope 21. The size of defective particles in the sample 14 is on the order of several tens of μm, and the resolvability of the microscope 21 is several hundred nm. Therefore, the defective particles can be regarded as point light sources. Thus, by finding the spread of the point image in the focal point position on the image point side, it is possible to determine the size of the point light source.

Figure 5:
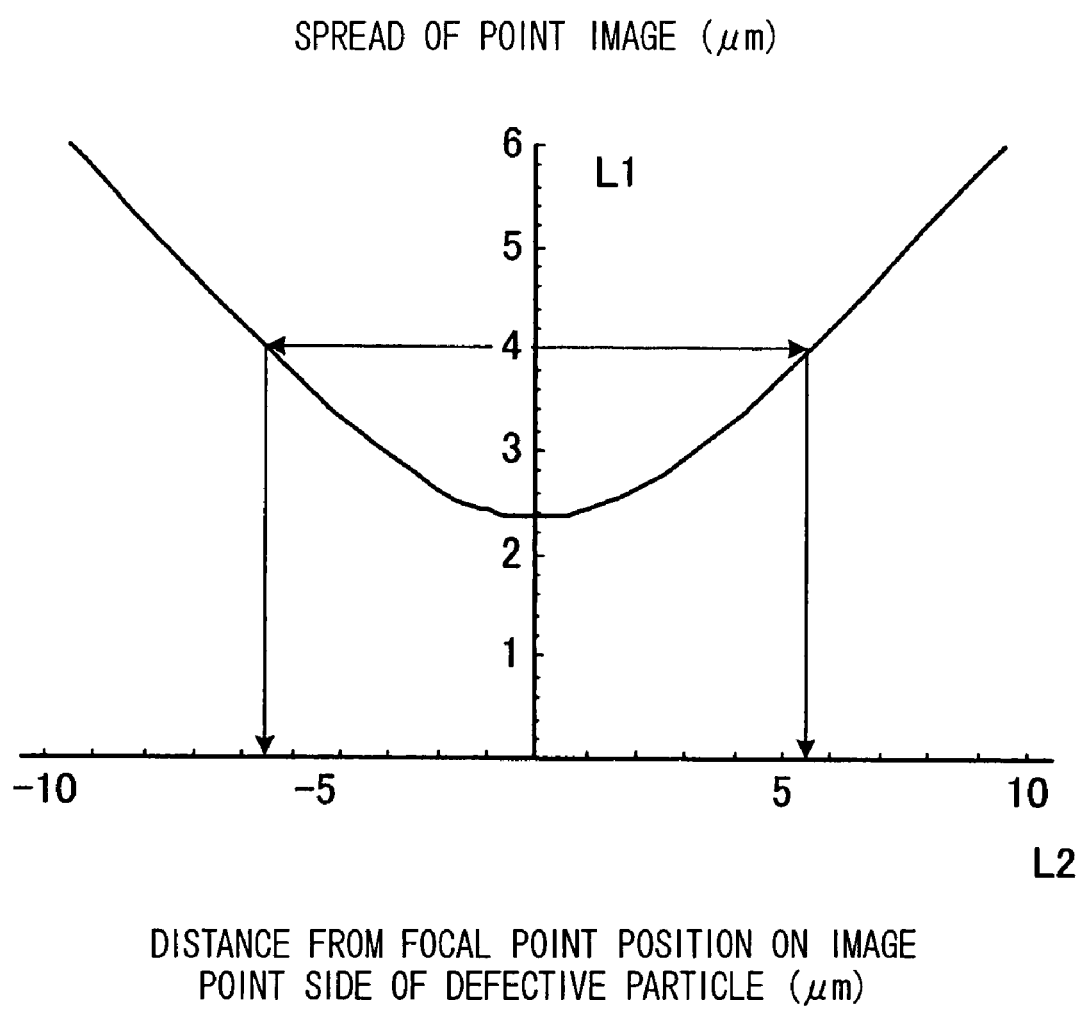
FIG. 5 is a diagram showing the relationship between the spread of a point image on the image point side in the focal point distance and the distance of a defective particle from the focal point length on the object point side.
Figure 6:
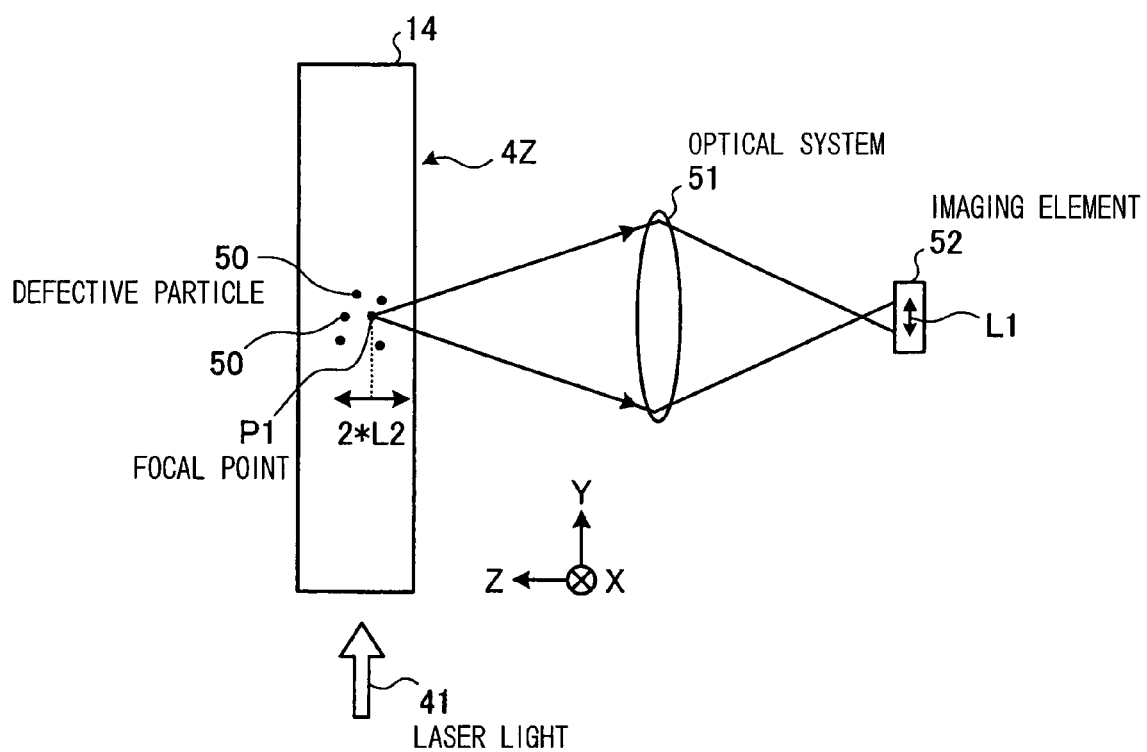
FIG. 6 is a schematic view illustrating the relationship between the spread of point images on the image point side in the focal point distance and the distance from the focal length on the object point side of a defective particle.
Figure 7:
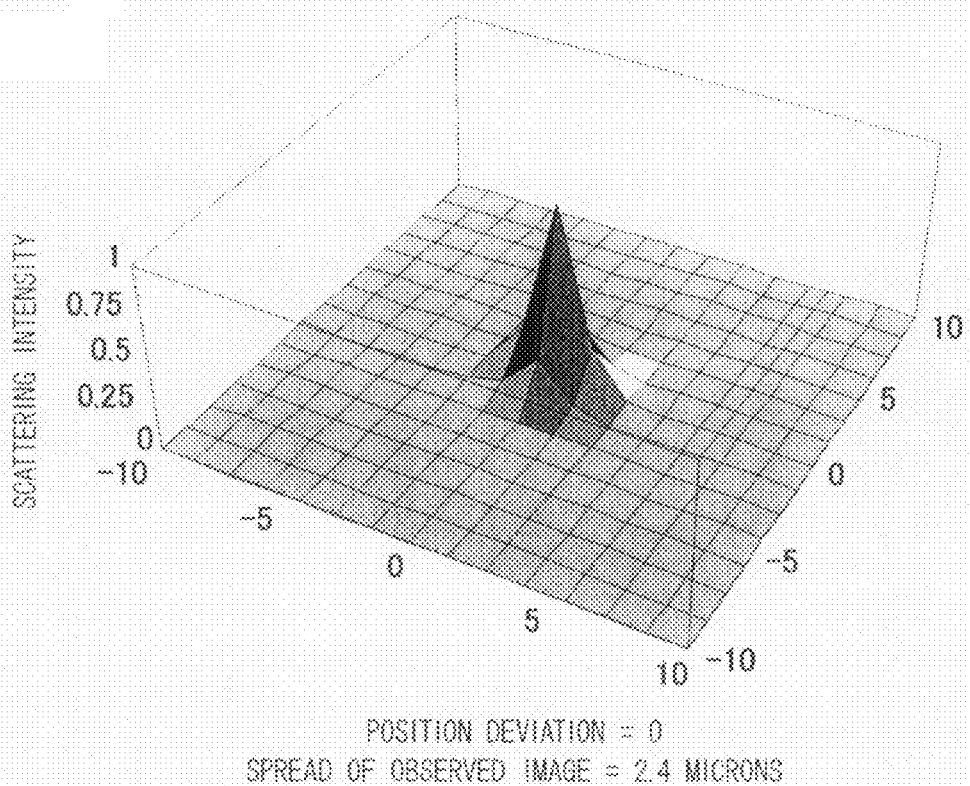
FIG. 7 is a view showing the scatter intensity distribution when the position deviation is 2.4 µm.
Figure 8:
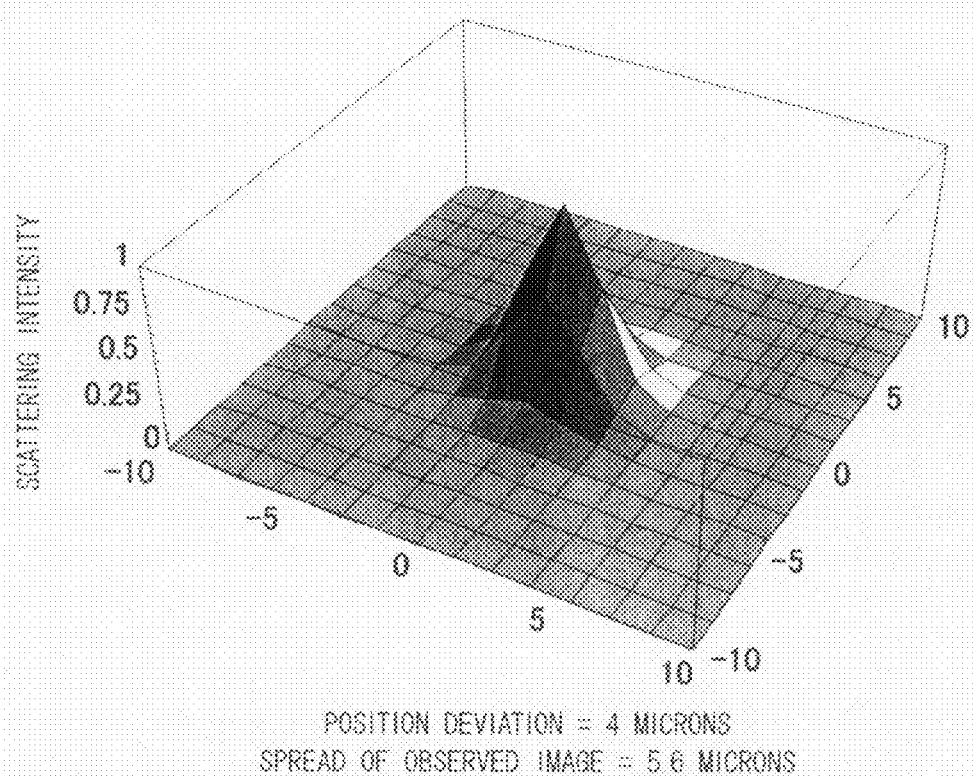
FIG. 8 is a view showing the scatter intensity distribution when the position deviation is 4 µm.
Figure 9:
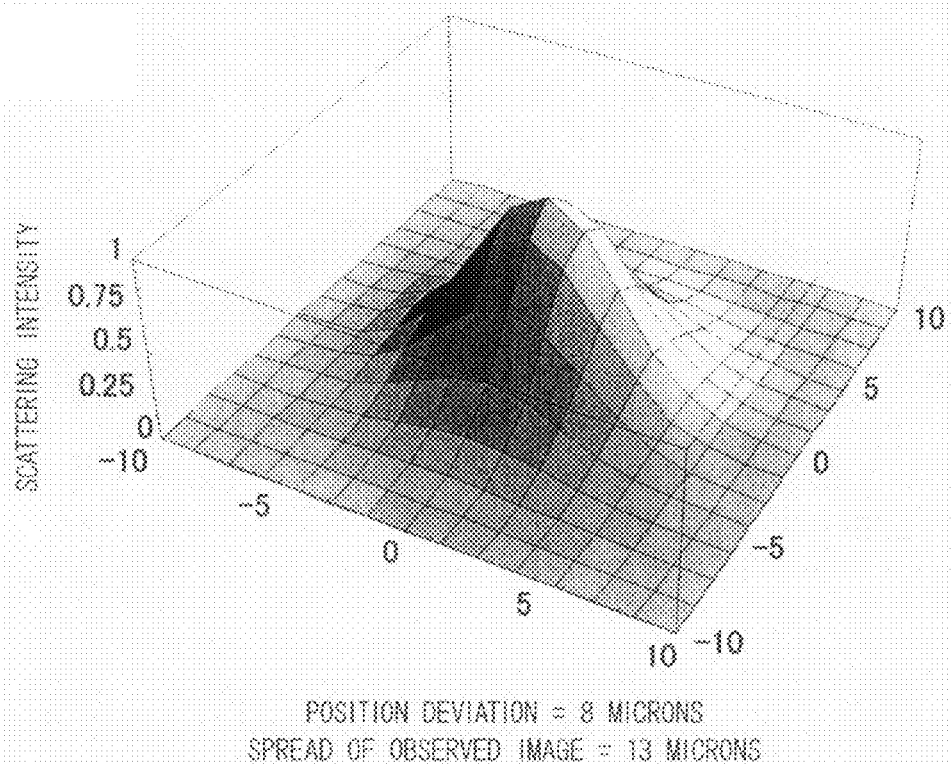
FIG. 9 is a view showing the scatter intensity distribution when the position deviation is 8 µm.
Figure 10:
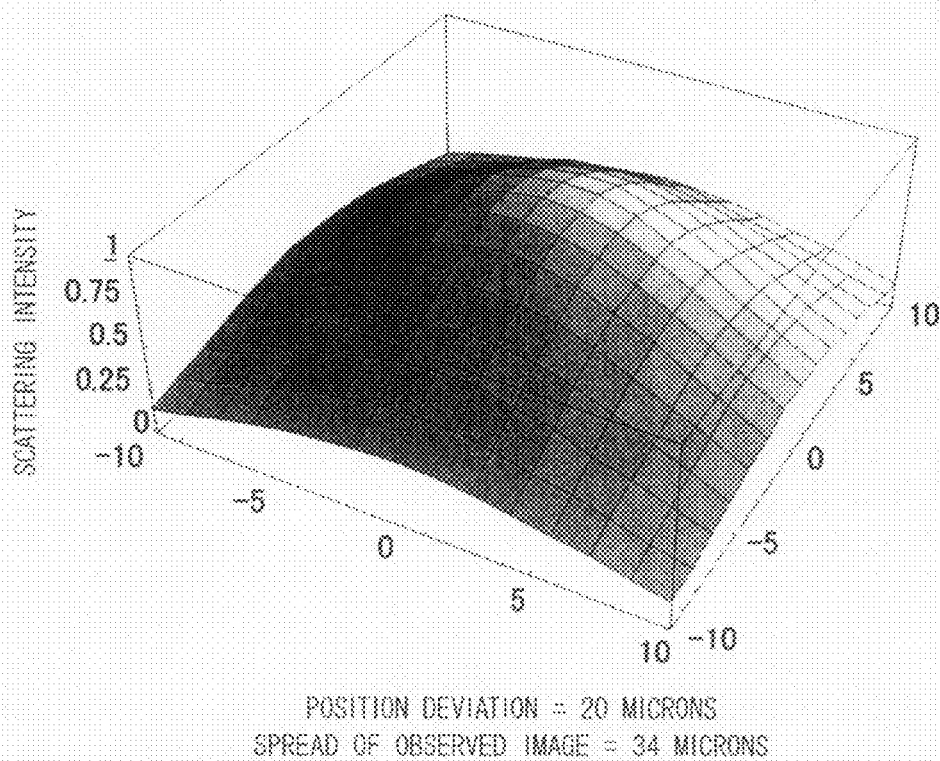
FIG. 10 is a view showing the scatter intensity distribution when the position deviation is 20 µm.

FIG. 5 is a diagram showing the relationship between the spread of a point image and the distance from the focal point position on the image point side to a defective particle. FIG. 6 is a schematic view showing the relationship between the focal portion on the object point side, defective particles, and the spread of a point image in the focal point position on the image point side. In FIG. 5 and FIG. 6, the defective particles 50 in the sample 14 form point images on an imaging element 52 by the optical system 51 of the microscope 21, and these point images have a spread L1. The relationship between this spread L1 and the distance between the defective particle 50 and the focal point P1 has a relationship as shown in FIG. 5. It can be seen that as a point image spreads, the position of the defective particle 50 deviates in the Z direction from the focal point position.

As shown in FIG. 7 to FIG. 10, the spread of a point image corresponds to the intensity distribution of the defective particle image. The intensity distributions shown in FIG. 7 to FIG. 10 show that when the position deviation of defective particles is 0 μm, 4 μm, 8 μm, and 20 μm, the spread of the observation image is 2.4 μm, 5.6 μm, 13 μm and 34 μm, respectively. Therefore, the position deviation computing portion 31, using the fact that this intensity distribution approximates a Gaussian distribution, performs fitting of the intensity distribution and a Gaussian distribution to perform determination of the intensity distribution, and can determine the position deviation of defective particles corresponding to this determined intensity distribution. The relationship between this intensity distribution and the position deviation of defective particles is stored as the position deviation table 26a. The position deviation computing portion 31, after determining the intensity distribution, obtains the position deviation of the defective particles by referring to the position deviation table 26a.

Figure 11:
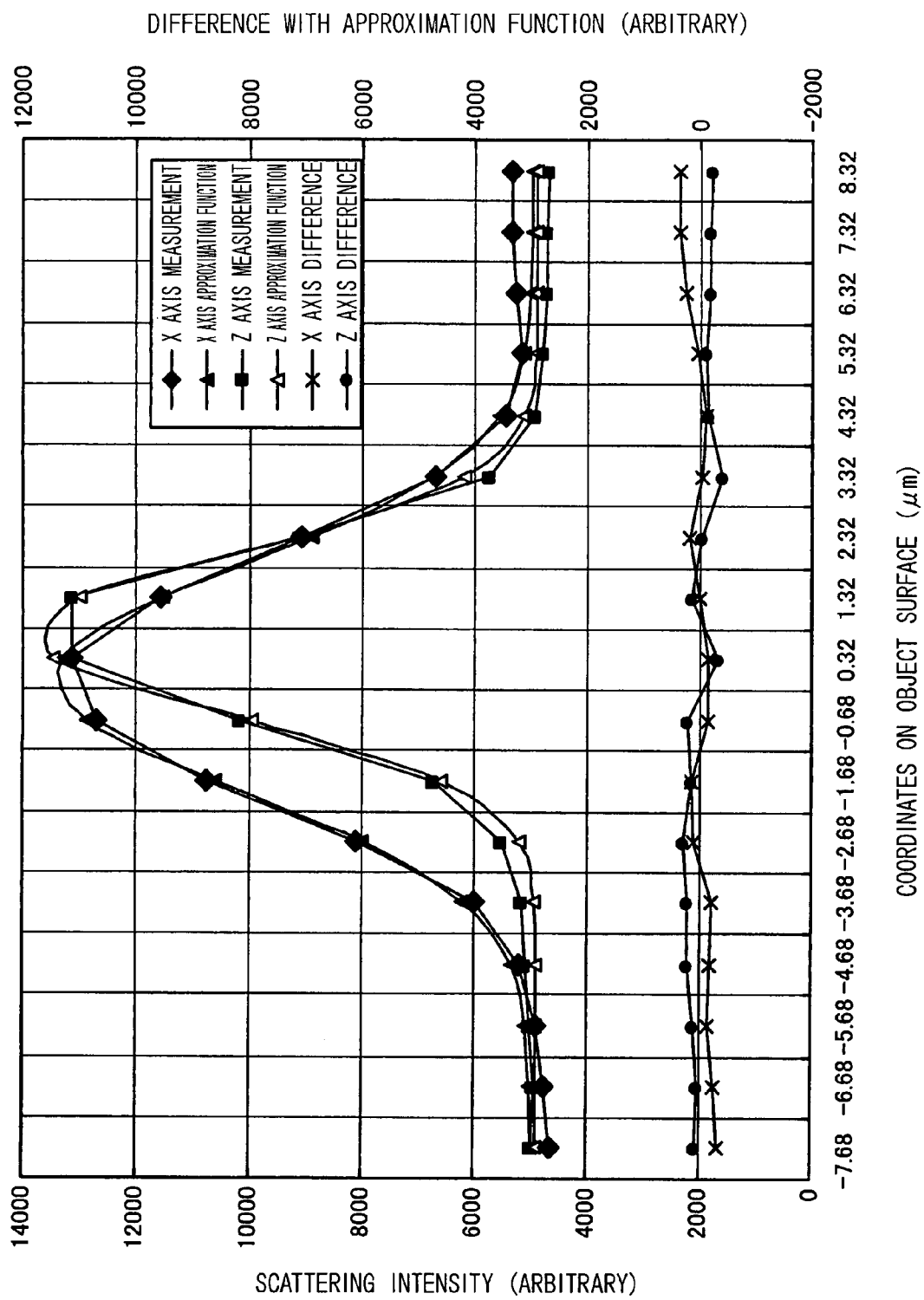
FIG. 11 is a diagram showing the fitting result of the scattering intensity distribution of defective particle images on the two-dimensional defective particle image and the Gaussian distribution.

FIG. 11 shows each fitting result in the X direction and the Z direction with respect to one defective particle image on the two-dimensional defective particle image, and the differential result with the fitting. As shown in FIG. 11, the intensity distribution fits well with the Gaussian distribution. From the X direction fitting result, the position of the defective particle is determined to be deviated 5.3 μm in the Y direction (depth direction) from the focal point position, and from the Z direction fitting result the position of the defective particle is determined to be deviated 3.72 μm in the Y direction (depth direction) from the focal point position. Aberration of the optical system 51 is also considered to affect the difference in the position deviation.

Figures 12, 13:
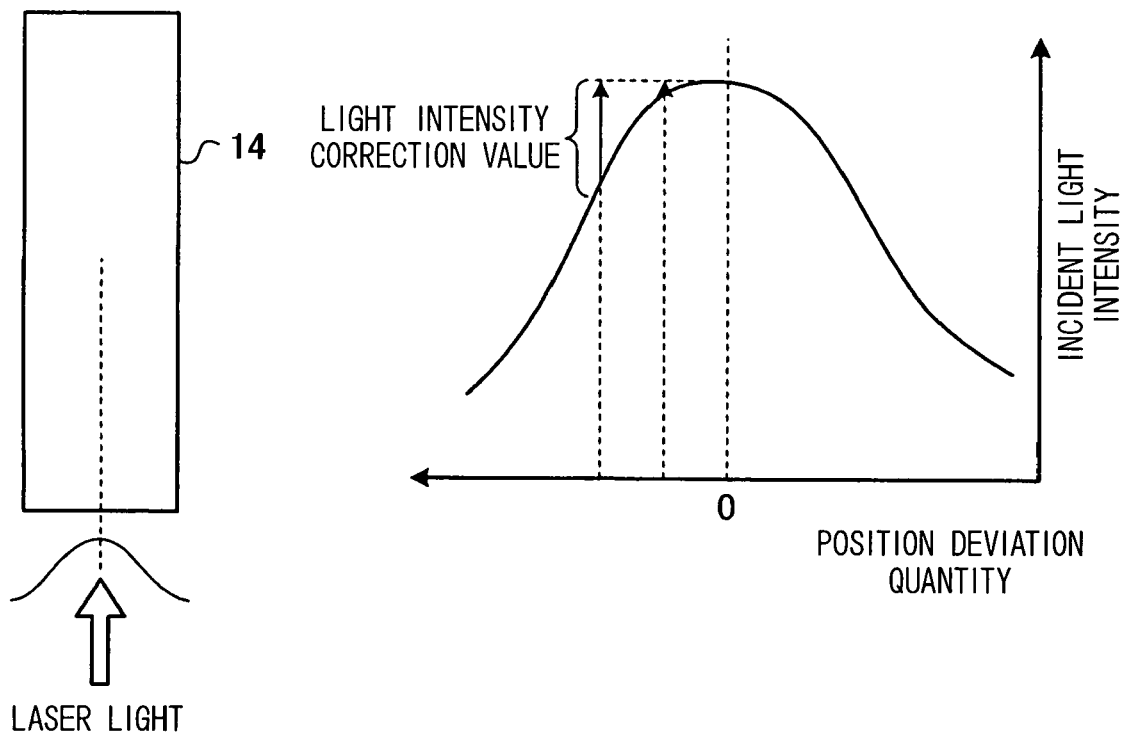
FIG. 12 is a diagram showing the relationship between the intensity distribution of the incident laser light and the correction of the scatter intensity.
FIG. 13 is a diagram showing an example of a position deviation table.

As shown in FIG. 12, the laser light that is made incident has an intensity distribution in a plane that is perpendicular to the axis of incidence, and due to this intensity distribution, defective particles of the same size have different scattering intensities. Therefore, it has not been possible to determine the size of a defective particle solely with scattering intensity. In the present embodiment, the position deviation computing portion computes the position deviation amount from the focal point position on the object point side. Therefore, as shown in FIG. 12, from the relationship between the position deviation amount and the incident light intensity distribution, the intensity correcting portion 32, irrespective of the position deviation amount, corrects the detected scattering intensity so as to be the same scattering intensity as when incident light intensity that is the same as when a defective particle exists on the axis of incidence is irradiated on the defective particle. Correction of the scattering intensity depending on the position deviation amount is performed referring to the intensity correction table 26b shown in FIG. 13. In the intensity correction table 26b is stored a correction coefficient for correcting the scattering intensity, corresponding to the position deviation amount. Since it is possible to remove differences in scattering intensity accompanying position deviation by performing such correction of the scattering intensity, the size determining portion 33 can determine the size of defective particles with only the magnitude of only the scattering intensity that is corrected.

Figure 14:
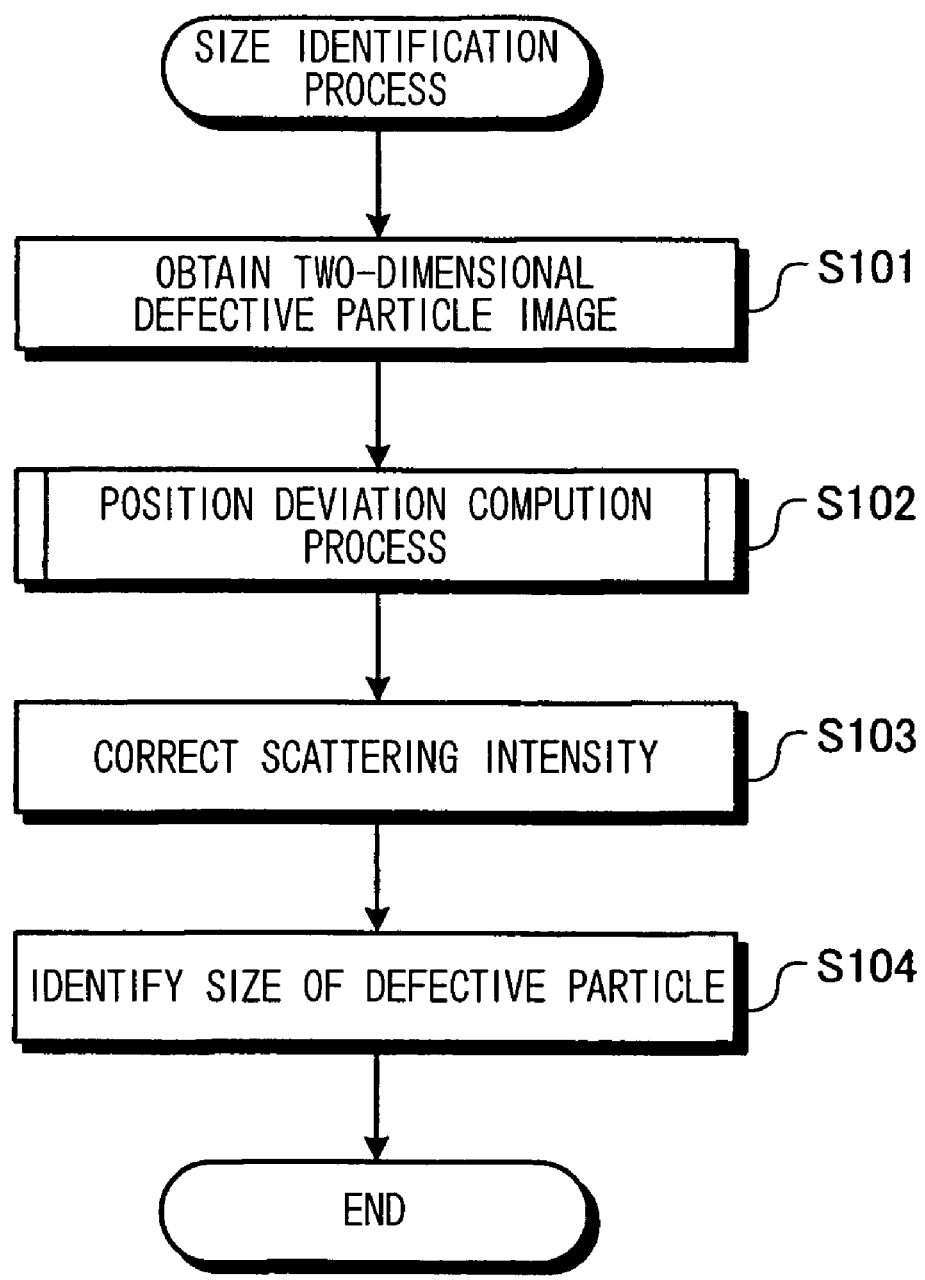
FIG. 14 is a flowchart that shows the size determining procedure that is performed by a control portion.

Here, the defective particle size determination process shall be described with reference to the flowchart shown in FIG. 14. In FIG. 14, first, the image processing portion 30 acquires a two-dimensional defective particle image (step S101). Then the position deviation computing portion 31 performs a position deviation computing process to compute the position deviation amount of a defective particle for each defective particle image of the two-dimensional defective particle image (step S102). Then, based on this position deviation amount, correction of the scattering intensity is performed so that the incident light intensity has no relation to the position deviation (step S103). Then, the size determining portion 33 determines the size of the defective particles based on the magnitude of the corrected scattering intensity (step S104), and the process is terminated. Note that the determination of the defective particle size may be performed with using a table in which is stored the relationship between the scattering intensity and the defective lattice size.

Figure 15:
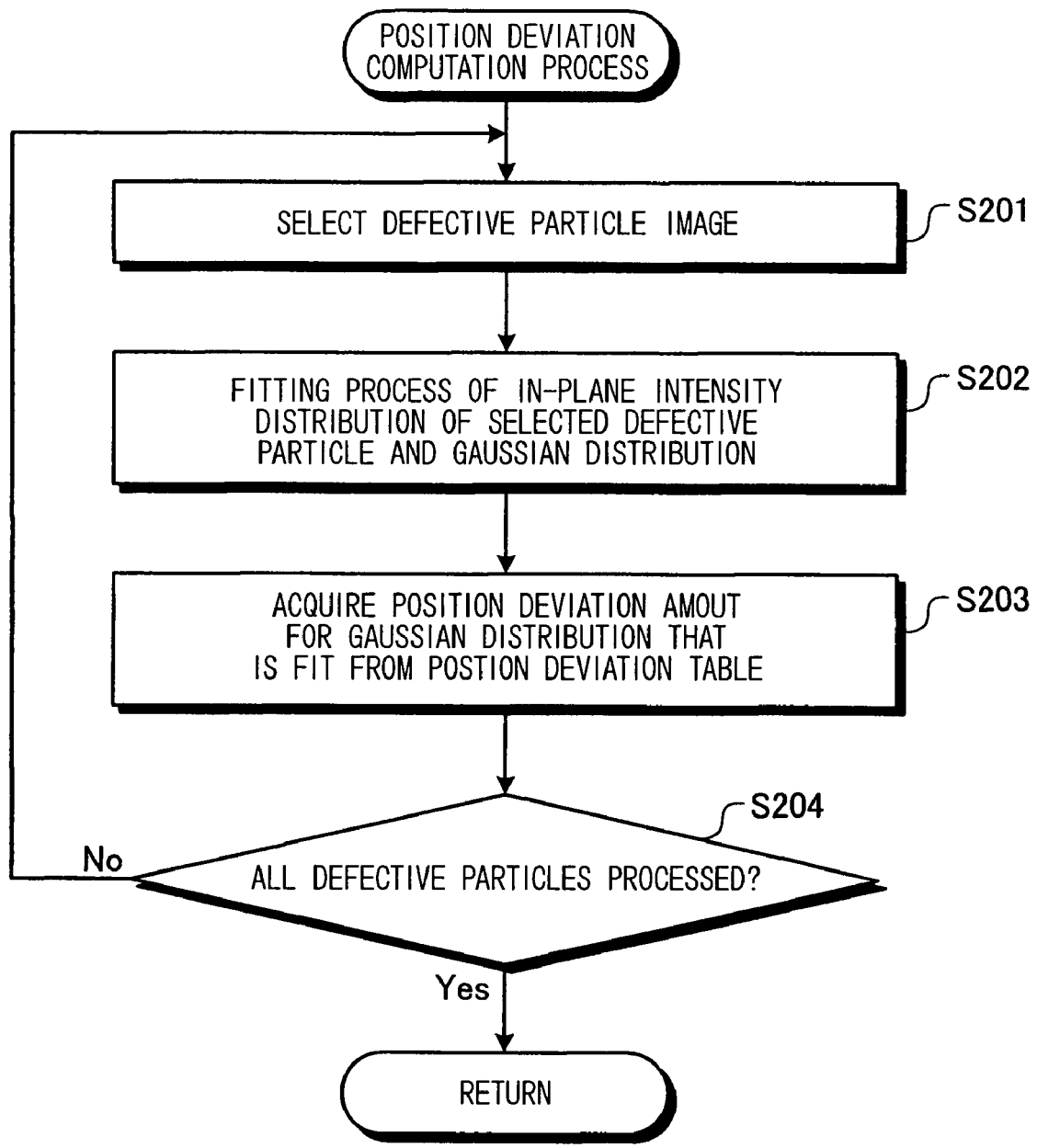
FIG. 15 is a detailed flowchart showing the position deviation computing procedure shown in FIG. 14.

FIG. 15 is a flowchart showing the processing steps of the position deviation computing process shown in step S102. As shown in FIG. 15, first, one defective particle image is selected from the two-dimensional defective particle image (step S201), and a process is performed of fitting the in-plane intensity distribution of the selected defective particle image and a Gaussian distribution (step S202). Then, the position deviation amount with respect to the fitted Gaussian distribution is acquired from the position deviation table 26a (step S203). Then, a judgment is made as to whether the processing has been performed on all of the defective particle images (step S204). In the case of the processing not being performed on all of the defective particle images ("NO" in step S204), the processing moves to step S201, the next defective particle image is selected, and the above process is repeated. In the case of the processing being performed on all of the defective particle images ("YES" in step S204), the processing returns to step S102.

Figure 16:
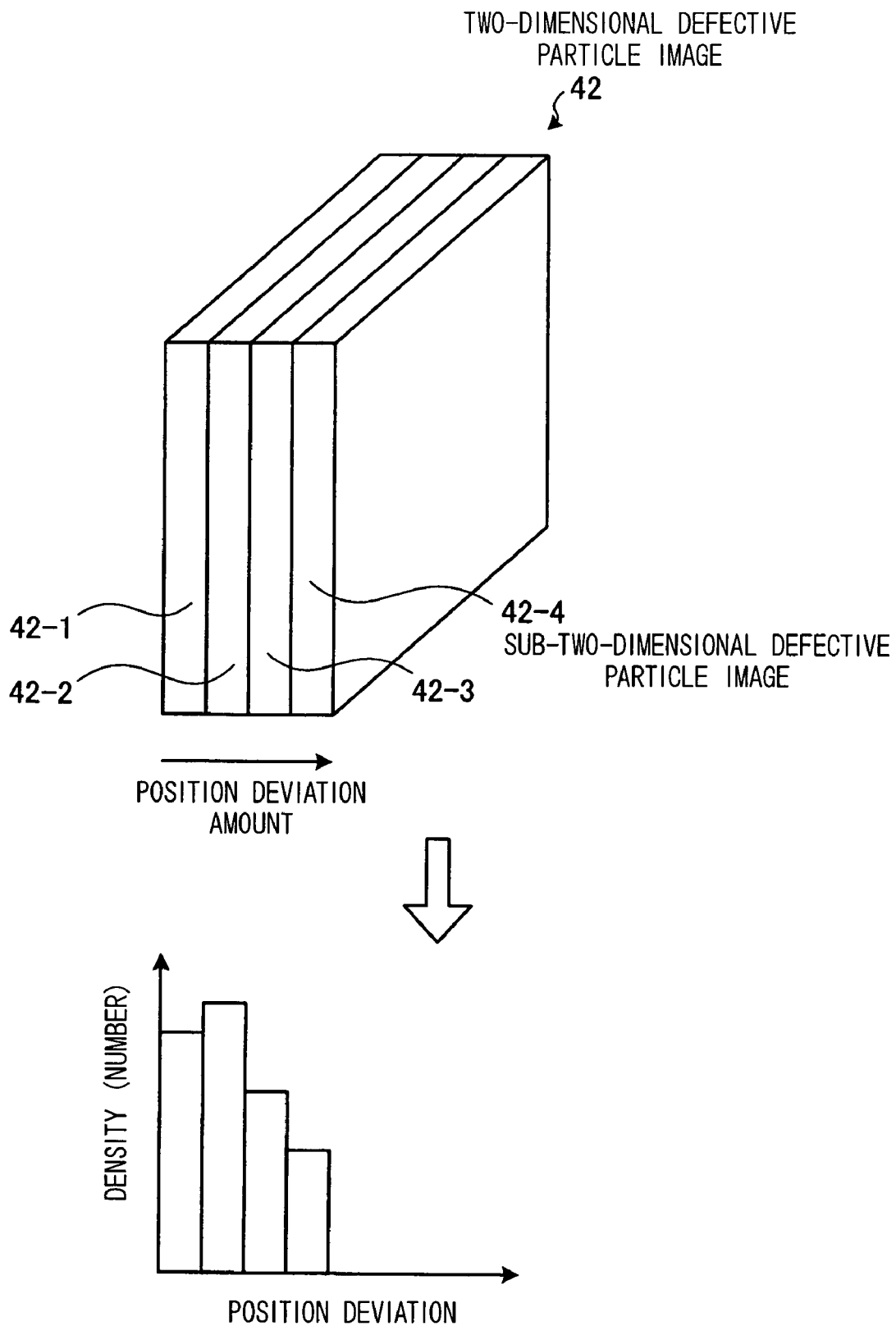
FIG. 16 is a view describing the process of finding the density distribution of defective particles with respect to the position deviation from the two-dimensional defective particle image.

Next, the process of computing density distribution of defective particles using the position deviation amount shall be described. The position deviation of defective particles found by the position deviation computing portion 31 given above is also used in computing density distribution of defective particles. As shown in FIG. 16, since the defective particle images on the two-dimensional defective particle image 42 each has a position deviation amount, they can be classified into a plurality of sub-two-dimensional defective particle images 42-1 to 42-4 according to the range of the position deviation amount. It is possible to measure the number of defective particles of each of the classified sub-two-dimensional defective particle images 42-1 to 42-4, and possible to obtain a distribution of the defective lattice number, that is, the density distribution, corresponding to the position deviation amount as shown in FIG. 16.

Figure 17:
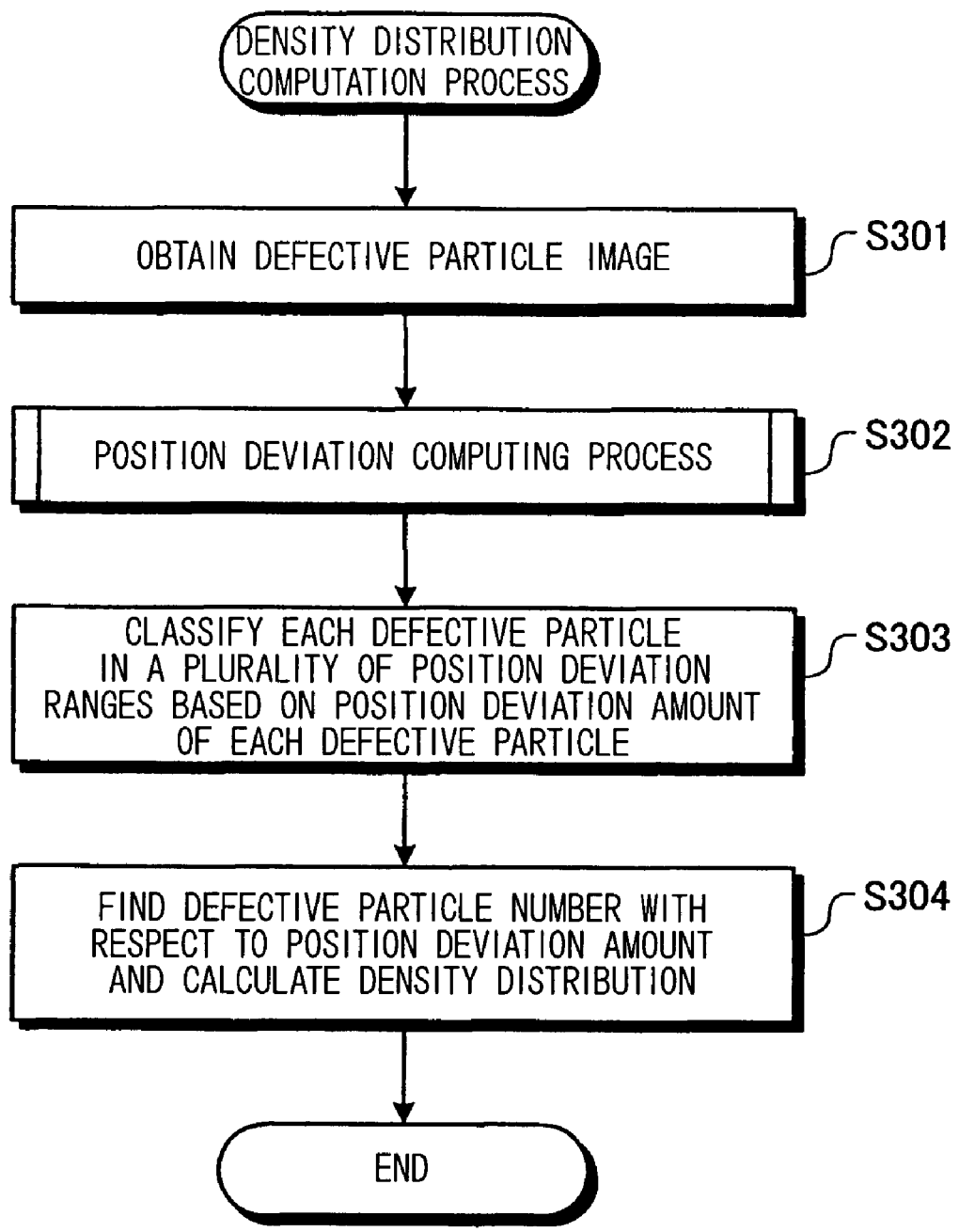
FIG. 17 is a flowchart that shows the density distribution computation procedure performed by a control portion.
Figure 18:
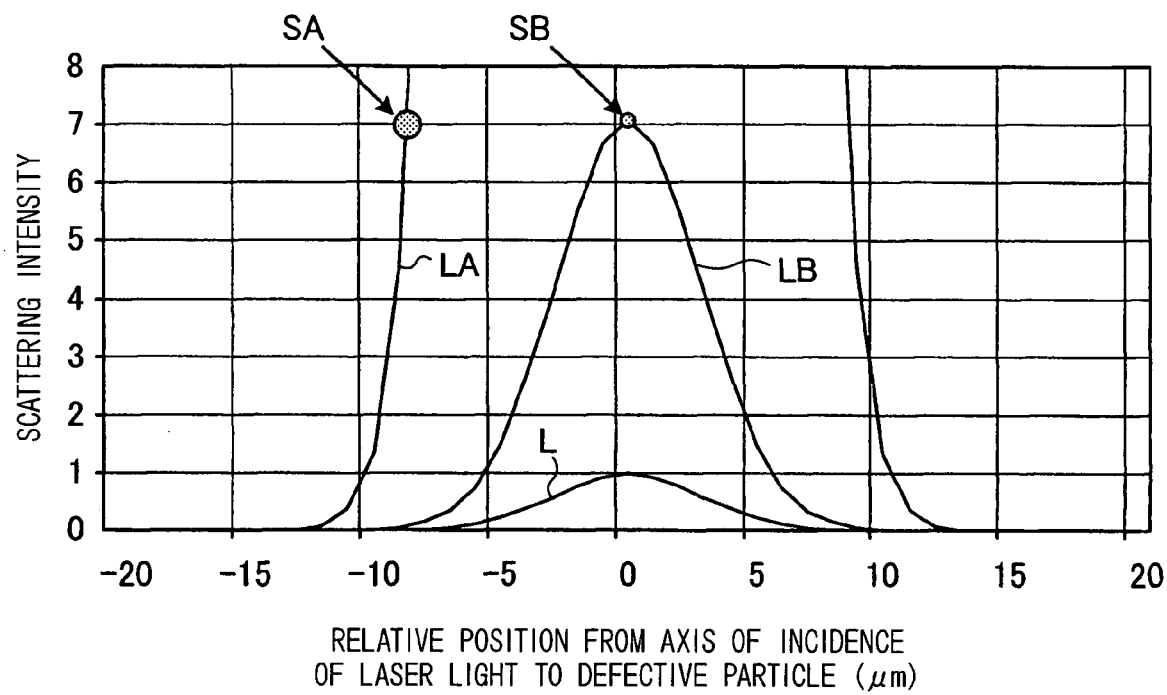
FIG. 18 is a diagram showing the relationship between the scatter intensity and the size of defective particles in the case of position deviation not being considered.

Here, based on the flowchart shown in FIG. 17, the processing procedure of computing the density distribution shall be described. In FIG. 17, first, the image processing portion 30 obtains a two-dimensional defective particle image (step S301). Then, similarly to step S102, a position deviation computing portion 31 performs a position deviation computing process to compute the position deviation amount of a defective particle for each defective particle image of the two-dimensional defective particle image (step S302). Then, a density distribution computing portion 34 classifies each defective particle in a plurality of position deviation ranges based on this position deviation amount (step S303), obtains the defective particle number with respect to the position deviation amount, calculates the density distribution (step S304), and terminates the processing. Note that the density distribution that is obtained in step S304 can be output on the monitor 24.

In the present embodiment, defective particles are regarded as point light sources and, using the relationship of the spread of a point image in the focal point position on the image point side and the position deviation of defective particles in the focal point position on the object point side, based on a two-dimensional defective particle image, the intensity distribution of the defective particle images is fit in a Gaussian distribution to obtain the position deviation amount of the defective particles. Based on this position deviation amount, the scattering intensity is corrected to determine the size of the defective particles or find the density distribution. Therefore, even without acquiring a cross-sectional image that is a plurality of two-dimensional defective particle images, it is possible to measure the size of defective particles or the density distribution of defective particles with a simple constitution in a short time at a high precision.

In the aforedescribed embodiment, the size of defective particles or the density distribution of defective particles was obtained based on a single two-dimensional defective particle image. However, a three-dimensional image may be obtained by taking a plurality of cross-sectional images with a comparatively large interval and applying the embodiment of this invention.

Also, in the aforedescribed embodiment, a semiconductor wafer was given as an example of the sample 14, but is not limited thereto, and the sample 14 may be a fluid such as a liquid or gas.

INDUSTRIAL APPLICABILITY

As described above, the defective particle measurement apparatus and defective particle measuring method are useful for a defective particle measurement apparatus and defective particle measuring method for measuring a defective particle in a sample such as a solid or fluid, and in particular are suited to a defective particle measurement apparatus and defective particle measuring method that measure defective particles in a semiconductor wafer.

The invention claimed is:

1. A defective particle measuring apparatus that irradiates focused laser light on a sample, images scattered light from the sample, and measures defective particles in the sample based on the image result, comprising
    a position deviation computing portion which, based on an in-plane intensity distribution of scattered light of each defective particle that is imaged, obtains a deviation from a focal point position on an image point side of the scattered light of the each defective particle and calculates a position deviation amount in a depth direction of the defective particle corresponding to the deviation from the focal point position,
    the defective particle measuring apparatus measuring characteristics of the defective particle based on the position deviation amount that is calculated by the position deviation computing portion.

2. The defective particle measuring apparatus according to claim 1, wherein the position deviation computing portion obtains the in-plane intensity distribution of the scattered light approximated to a Gaussian distribution.

3. The defective particle measuring apparatus according to claim 2, wherein the position deviation computing portion obtains the in-plane intensity distribution of the scattered light approximated to a Gaussian distribution.

4. A defective particle measuring apparatus that irradiates focused laser light on a sample, images scattered light from the sample, and measures defective particles in the sample based on the image result, the defective particle measuring apparatus comprising:
    a position deviation computing portion which, based on an in-plane intensity distribution of scattered light of each defective particle that is imaged, obtains a deviation from a focal point position on an image point side of the scattered light of the each defective particle and calculates a position deviation amount in a depth direction of the defective particle corresponding to the deviation from the focal point position;
    a light intensity correcting portion which corrects the light intensity of the scattered light of the defective particle corresponding to the position deviation amount in the depth direction; and
    a size determining portion which determines the size of the defective particle based on the light intensity corrected by the light intensity correcting portion.

5. A defective particle measuring apparatus that irradiates focused laser light on a sample, images an in-plane intensity distribution of scattered light from within the sample, and measures defective particles in the sample, the defective particle measuring apparatus comprising:
    a position deviation computing portion which, based on an in-plane intensity distribution of scattered light of each defective particle that is imaged, obtains a deviation from a focal point position on an image point side of the scattered light of the each defective particle and calculates a position deviation amount in a depth direction of the defective particle corresponding to the deviation from the focal point position; and
    a density computing portion that divides the position deviation amount in the depth direction into a plurality of ranges, obtains the number of defective particles that exist within each range, and computes a distribution density of the defective particles in the depth direction from a focal point position on an object point side of an imaging optical system.

6. The defective particle measuring apparatus according to claim 5, wherein the position deviation computing portion obtains the in-plane intensity distribution of the scattered light approximated to a Gaussian distribution.

7. A defective particle measuring method that irradiates focused laser light on a sample, images scattered light from the sample, and measures defective particles in the sample based on the image result, the defective particle measuring method comprising position deviation computing steps of:
    obtaining a deviation from a focal point position on an image point side of scattered light of each defective particle based on an in-plane intensity distribution of the scattered light of the each defective particle that is imaged; and calculating a position deviation amount in a depth direction of the defective particle corresponding to the deviation from the focal point position,
    characteristics of the defective particle being measured based on the position deviation amount that is calculated by the position deviation computing steps.

8. The defective particle measuring method according to claim 7, wherein the position deviation computing steps include obtaining the in-plane intensity distribution of the scattered light approximated to a Gaussian distribution.

9. A defective particle measuring method that irradiates focused laser light on a sample, images scattered light from the sample, and measures defective particles in the sample based on the image result, the defective particle measuring method comprising: position deviation computing steps of
    obtaining a deviation from a focal point position on an image point side of scattered light of each defective particle based on an in-plane intensity distribution of the scattered light of the each defective particle that is imaged, and
    calculating a position deviation amount in a depth direction of the defective particle corresponding to the deviation from the focal point position;
    a light intensity correcting step of correcting light intensity of the scattered light of the defective particle corresponding to the position deviation amount in the depth direction; and
    a size determining step of determining a size of the defective particle based on the light intensity corrected by the light intensity correcting step.

10. The defective particle measuring method according to claim 9, wherein the position deviation computing steps include obtaining the in-plane intensity distribution of the scattered light approximated to a Gaussian distribution.

11. A defective particle measuring method that irradiates focused laser light on a sample, images an in-plane intensity distribution of scattered light from within the sample, and measures defective particles in the sample, the defective particle measuring method comprising:

position deviation computing steps of obtaining a deviation from a focal point position on an image point side of scattered light of each defective particle based on an in-plane intensity distribution of the scattered light of the each defective particle that is imaged, and calculating a position deviation amount in a depth direction of the defective particle corresponding to the deviation from the focal point position; and density computing steps of dividing the position deviation amount in the depth direction into a plurality of ranges, obtaining the number of defective particles that exist within each range, and computing a distribution density of the defective particles in the depth direction from a focal point position on an object point side of an imaging optical system.

12. The defective particle measuring method according to claim 11, wherein the position deviation computing steps include obtaining the in-plane intensity distribution of the scattered light approximated to a Gaussian distribution.

* * * * *